United States Patent [19]

Hollibush et al.

[11] Patent Number: 5,068,107

[45] Date of Patent: Nov. 26, 1991

[54] POLYMERIC ORTHODONTIC MEMBERS AND ORTHODONTIC TREATMENT METHOD

[75] Inventors: Daniel J. Hollibush, Kansasville, Wis.; Jeffery Fasnacht, Columbus, Ind.; Edward G. Eeg, Racine, Wis.

[73] Assignee: Ortho-Vacon, Inc., Kansasville, Wis.

[21] Appl. No.: 286,316

[22] Filed: Dec. 16, 1988

Related U.S. Application Data

[63] Continuation-in-part of Ser. No. 143,748, Jan. 14, 1988, abandoned.

[51] Int. Cl.$^5$ .............................................. A61F 13/00
[52] U.S. Cl. .................................... 424/435; 424/422; 424/423; 424/434
[58] Field of Search ........................................... 424/435

[56] References Cited

U.S. PATENT DOCUMENTS

| | | | |
|---|---|---|---|
| 3,205,576 | 9/1965 | Wallshein | 32/14 |
| 4,175,326 | 11/1979 | Goodson | 424/435 |
| 4,568,535 | 2/1986 | Loesche | 424/435 |
| 4,569,837 | 2/1986 | Suzuki et al. | 424/435 |

*Primary Examiner*—Thurman K. Page
*Assistant Examiner*—Leon R. Horne
*Attorney, Agent, or Firm*—Jansson & Shupe, Ltd.

[57] ABSTRACT

An improved elastic orthodontic member and treatment method for preventing and treating certain dental diseases often associated with or increased by normal orthodontic treatment. The orthodontic member is an orally-acceptable elastic polymeric material having a dentally-active pharmacological agent uniform throughout the polymeric material as an in situ constituent of polymeric-member formation from a homogeneous mixture of polymeric material and pharmacological agent. Without compromising orthodontic force-applying elasticity, the orthodontic member provides release of pharmacological agent in an intraoral environment in therapeutically-acceptable concentrations over an extended period which is substantially commensurate with the useful life of force-applying elasticity of said orthodontic member.

9 Claims, No Drawings

POLYMERIC ORTHODONTIC MEMBERS AND ORTHODONTIC TREATMENT METHOD

RELATED APPLICATION

This is a continuation-in-part of copending Ser. No. 143,748 now abandoned, entitled "Improved Polymeric Orthodontic Members With Dentally-Active Pharmacological Agents," filed Jan. 14, 1988, by Daniel J. Hollibush, Jeffery Fasnacht, and Edward G. Eeg, the applicants herein.

FIELD OF THE INVENTION

This invention is related generally to dental care and, more particularly, to the prevention and treatment of dental disease in patients during the course of orthodontic treatment.

BACKGROUND OF THE INVENTION

The prevention and treatment of oral diseases, such as gingivitis, periodontitis and dental caries, typically are much more difficult during a course of orthodontic treatment than at other times, for reasons which are quite apparent. The continuous presence of brackets, wires and other orthodontic paraphernalia in the mouth interferes with normal oral hygiene.

It is well known that dental disease is caused in major part by failure to frequently and completely remove food residues from positions against the teeth and gums, and/or by the presence of accumulated plaque. Removal of food residues is very important if dental caries and gum disease are to be avoided. And, accumulation of plaque on teeth is particularly undesirable because it leads to gingivitis, which, in turn, may progress to periodontitis.

Orthodontic braces in certain situations make it difficult at best to reach and remove food and to remove or control plaque by the normal mechanical techniques, such as brushing, flossing, and water irrigating. Toothbrush bristles cannot readily reach all areas of the teeth, and dental floss cannot reach the areas between the teeth adjacent to the gums or portions of the gingival sulci.

Not only are mechanical cleaning procedures impeded or blocked, but orthodontic braces are by nature food traps which predispose the teeth to development of dental caries and accumulation of plaque. Furthermore, the shifting of tooth positions during orthodontic treatment itself further predisposes a patient to development of gingivitis.

Because of difficulty of mechanical cleaning during a course of orthodontic treatment, chemical cleaning and plaque control take on greater importance.

A wide variety of dentally-active pharmacological agents are known, including antiseptic agents, anti-plaque agents and anticaries agents. Examples include: certain halide salts, particularly specific fluorides and chlorides such as stannous fluoride, sodium fluoride, and sodium chloride; fluorides such as sodium fluoride with soluble pyrophosphates such as a mixture of tetrasodium pyrophosphate and disodium dihydrogen pyrophosphate; chlorhexidine digluconate; and sanguinarine.

While the nature of the dental therapeutic benefits of these examples need not be reviewed in detail here, a few comments may be helpful.

The anti-caries and anti-gingivitis effects of certain fluorides and chlorides are well known. Stannous fluoride is known to prevent plaque bonding and thus prevent plaque buildup. The soluble pyrophosphates have been shown, in combination with sodium fluoride, to enhance the interruption of the transformation of amorphous calcium phosphate into dental calculus.

Chlorhexidine digluconate, a water-soluble compound, has been shown to be effective against periodontal disease. It has a significant plaque-inhibiting effect, Contributes to plaque breakdown, and is a potent suppressor of *Streptococcus Mutans*, which is implicated in dental caries. It is known to be effective in reducing periodontal inflammation. Sanguinarine, which has an affinity for plaque, has been demonstrated to have a significant anti-plaque effect. It has been shown to be superior to certain other therapeutic agents in inhibiting salivary glycolysis, which is used as a predictor of the effectiveness of antiplaque agents.

These and other therapeutic agents may be applied to the teeth and gingiva in efficacious concentrations by means of toothpastes, mouthwashes and the like. However, such periodic applications may not completely reach the gingival sulci and other positions where disease is most likely, including tooth surfaces against which orthodontic paraphernalia is located. And, more significantly, such applications are transient, occurring between extended periods in which no therapeutic agent is introduced and previously introduced therapeutic agents are quickly diluted and dissipate.

Increasing the concentration of a dentally-active agent periodically introduced into the mouth, as in a mouthwash, may have the effect of extending somewhat the period of efficacy. But considering the lengthy period between successive introductions of such agents, even with a rigorous mouthwashing schedule, any such extending effect may not be very significant, unless the therapeutic agent has particular affinity for dental surfaces.

Furthermore, certain dentally-active pharmacological agents have negative side effects when introduced into the mouth or ingested in high concentrations, ruling out or limiting their use in such relatively high concentrations.

During a course of orthodontic treatment, the current practice is to introduce dentally-active pharmacological agents by mouthwashes several times daily. This practice overcomes the disadvantage of transience, mentioned above, only slightly, and only to the extent that frequency and regularity are emphasized to the inconvenience of the orthodontic patient.

Other means for introducing therapeutic agents into the intraoral environment have been proposed. Among these are the oral dispensing devices of U.S. Pat. Nos. 4,175,326 and 3,205,576, which relate to polymeric members having coatings or substances entrapped in spaces of various kinds such as the lumens of hollow fibers, surface caches, and the like. In such devices, the therapeutic substance will be released quickly in the intraoral environment and/or the release will be difficult to control. In some cases, not only could pharmacological agents be released much too quickly, but such agents, particularly certain agents, would be in too high a concentration in the mouth.

One critical characteristic of various orthodontic elastic polymeric members, such as elastic bands, elastomeric ligature ties or "threads," elastomeric chains, separators, super ties, and Steiner rotation wedges, is their elastic qualties—that is, their ability to apply force for various purposes in the mouth. Orthodontics involves the use of a variety of orthodontic braces, wires, and other orthodontic elements mounted in the mouth for the specific purpose of moving teeth away from positions of malocclusion. Such moving action itself and the appropriate securement of orthodontic paraphernalia are dependent on the force-applying ability of orthodontic elastic polymeric members. That is a principal reason why orthodontists replace such elastic polymeric members on a regular basis.

Replacement is required when the useful force-applying life of the elastic polymeric member, or much of such life, has passed. The length of such useful life is dependent on many factors. In the above-mentioned patents having polymeric members used to hold and dispense therapeutic substances, there is no correlation whatever between the release (typically very quick) of such substances and any force-applying capability for orthodontic purposes.

Indeed, U.S. Pat. No. 4,175,326 has polymeric members which are not elastic and therefore have no force-applying ability or life, or for that matter any orthodontic use.

Orthodontic elastic bands of the prior art have included flavoring. These include the coated bands of U.S. Pat. No. 3,205,576 mentioned above, the coating of which is released throughout the mouth in a "pump-like" action (col. 3, line 2), and the elastic bands of allowed copending Ser. No. 023,716, of Jeffery Fasnacht, an inventor herein, which have been in use. The latter include flavoring as an in situ constituent of elastic band formation from a homogeneous mixture of elastomer and flavoring substance.

There is a need for an improved orthodontic elastic polymeric member which, throughout its useful orthodontic force-applying life, provides a continuous acceptable level of therapeutic substance release immediately on the dental surface requiring such treatment, that is, immediately at the site of the orthodontic paraphernalia. There is a need for an improved method for prevention and treatment of dental disease during orthodontic treatment.

OBJECTS OF THE INVENTION

It is an object of this invention to provide an improved means for application of dentally-active pharmacological agents to the teeth and gingiva which overcomes problems and shortcomings of the prior art.

Another object of this invention is to provide an improved means for preventing an increased incidence of dental disease during a course of orthodontic treatment.

Another object of this invention is to provide an improved means for treating dental disease in patients undergoing orthodontic treatment.

Another object of this invention is to provide a method and means for substantially non-interrupted application of dentally-active pharmacological agents to the teeth and gingiva during a course of orthodontic treatment.

Another object of this invention is to provide a method and means for providing continuous release of a therapeutic substance immediately at the sites of greatest need in an orthodontic patient, and to provide such release at a relatively steady acceptable low level from an elastic polymeric orthodontic member throughout the useful force-applying life of such orthodontic member.

Another object of this invention is to use orthodontic paraphernalia as a means for substantially continuous introduction of dentally-active pharmacological agents to the teeth and gingiva during orthodontic treatment.

Another object of this invention is to provide means to increase the time during which dental therapeutic agents are in the mouth without increasing the concentrations of such agents in the mouth.

Still another object of this invention is to provide a more constant level of dentally-active agents in the mouth of orthodontics patients.

These and other important objects will be apparent from the following descriptions.

SUMMARY OF THE INVENTION

This invention involves an improved polymeric elastic orthodontic member of the type for intraoral mounting adapted to serve as a source of one or more dentally-active pharmacological agents, for substantially continuous application of such agents to the teeth and gingiva. Such improved polymeric elastic orthodontic members overcome certain problems in the prior art and provide an improved means and method for prevention and treatment of dental diseases of various kinds during a course of orthodontic treatment.

The improved polymeric elastic orthodontic member of this invention may be in a variety of well-known forms attached as part of normal orthodontic paraphernalia to the teeth and/or to orthodontic braces, wires, and other orthodontic elements. Such forms include elastic bands, elastomeric ligature ties and threads, elastomeric chains, separators, super ties, and Steiner rotation wedges, to give some common examples.

The orthodontic member of this invention is a substantially homogeneous polymeric elastic member formed of an orally-acceptable elastic polymeric material with a dentally-active pharmacological agent or agents uniform throughout the polymeric elastic material as an in situ constituent of polymeric-member formation from a homogeneous mixture of said polymeric material and said pharmacological agent. "In situ," as used herein, means that the pharmacological agent or agents, or a carrier composition for such agent or agents, is involved in original forming and curing of the polymeric piece, as opposed to impregnation or other deposit during subsequent manufacturing of the rubber-like orthodontic members.

The result of this is that, without compromising orthodontic force-applying elasticity, the orthodontic member provides release of the pharmacological agent in an intraoral environment in therapeutically acceptable concentrations during an extended period which is substantially commensurate with the useful life of force-applying elasticity of said orthodontic member. Indeed, the release occurs even as the force-applying elasticity of such members degrades over time; therefore, as long as the elastic strength is such that replacement is not mandated, release of pharmacological agent will continue.

Such pharmacological agents are releasable from the polymeric elastic materials in the intraoral environment over extended periods in therapeutically-acceptable amounts and concentrations. Such continuing low-level release of pharmacological agents is immediately at the sites of greatest need, that is, the tooth surfaces where the orthodontic paraphernalia is located, which is where dental disease is most apt to occur.

The dentally-active pharmacological agents are released from the polymeric elastic orthodontic members at a position immediately adjacent to the teeth and gingiva and are carried by oral fluids to the teeth and gingiva. This release and presence over prolonged periods allows such agents to reach and remain in the gingival sulci, in position to be most effective in preventing or treating periodontal disease.

The improved polymeric elastic orthodontic members of this invention, like any orthodontic elastic member, are replaced from time to time to provide a fresh and continuous supply of dentally-active pharmacological agents. Such replacement is done, of course, so that the elastic members in use will have suitable force-applying properties. One example is replaceable elastic bands. Such bands, when removed, discarded and replaced every few hours, enhance the continuous application of therapeutic agents and provide suitable force for the intended purposes. Other orthodontic elastics made in accordance with this invention may be replaced less frequently, usually by the orthodontist during regular visits.

Because of the substantially continuous application of dentally-active pharmacological agents directly to the teeth and gums, gingivitis and periodontitis may be treated more easily while avoiding the use of the large amounts of agents which are required by other methods of treatment. Because the application is continuous, concern about dilution is minimized, and high concentrations are not needed to prolong efficacy. And, in view of the low concentrations and small amounts which are present, ingestion concerns are reduced or eliminated and the risk of other side effects is reduced.

The use of the polymeric elastic orthodontic members of this invention during a course of orthodontic treatment can tend to reduce the incidence of dental caries, and reduce accumulation of dental plaque thereby reducing the likelihood of development of gingivitis and its progression to periodontitis And, treatment of dental disease may also be improved. Thus, the incidence of unfavorable outcomes during orthodontic treatment is reduced.

The intraoral polymeric elastic orthodontic member of this invention preferably has as its polymeric material natural rubbers, natural-synthetic rubbers, synthetic rubber, and thermoplastic polymeric materials, or blends thereof.

Different types of elastic polymeric materials are preferred for different orthodontic forms. For some forms, the elasticity must be greater than for others. One preferred material for forms such as ligature ties, are orally-acceptable polyether-type urethanes. For certain others, such as elastic bands, elastomeric materials such as natural rubber, natural-synthetic rubber, synthetic rubber, certain thermoplastic elastic polymeric materials, and blends thereof are highly preferred. Highly preferred elastomers include natural rubber (polyisoprene), natural-synthetic rubbers, which are generally similar to natural rubber, synthetic rubbers (such as neoprene, butyl and polybutadiene), and blends thereof.

In addition to such rubbers, some specific examples of acceptable elastic polymeric materials, without particular regard to the orthodontic application, are polyurethane elastomers such as those sold by Dow Chemical Company, Midland, Mich., as PELLATHANE 2363-80A and 2363-75A, and that sold as MOBAY 480-F by Mobay Chemical Company, St. Louis, Mo., and plasticized polyethylene.

The choice of a suitable elastic polymeric material will depend on several things, including the orthodontic form or application, the nature of the composition to be dispersed in it and released from it, including the therapeutic agent, and desired release characteristics. How long the polymeric elastic member is likely to remain in the mouth and the extent of its elastic characteristics are important are factors which must be considered.

As used herein, "polymeric" refers to natural or synthetic materials formed of one or more polymers, that is, organic chemical compounds in which each molecule is made up of simpler molecules strung together. "Elastomer" and "elastic" refers to polymeric materials having rubber-like elastic properties, that is, resilience such that they return to their original shape after stretching or compression.

Release characteristics can be varied in a number of ways, by an appropriate selection of a manufacturing method, by the extent of curing, by the choice of carrier compositions, by the amount of carrier composition, and in other ways. Appropriate choices will be apparent to those skilled in the art who familiar with this invention.

The dentally-active pharmacological agent is in, or by itself is, the composition which is dispersed in the polymeric material. In preferred embodiments, such dispersed composition is present in an amount no more than about 30 parts by weight per 100 parts of the polymeric material. Greater amounts of dispersed compositions within polymeric materials, particularly elastomeric materials, often tend to substantially interfere with certain qualities of such polymeric materials, especially their elastic qualities.

The dentally-active pharmacological agents useful in this invention include the halide salts, chlorhexidine digluconate, soluble pyrophosphates, sanguinarine, quaternary ammonium antiseptics, phenolic compounds, and mixtures thereof. Some specific examples of suitable halide salts are stannous fluoride, sodium fluoride, sodium chloride, and domiphen bromide; examples of soluble pyrophosphates are tetrasodium pyrophosphate and disodium dihydrogen pyrophosphate; an example of suitable quaternary ammonium antiseptics is benzalkonium chloride; and examples of suitable phenolic compounds are sec-amyltricresol and eugenol (an analgesic).

The halide salts are known as anticaries and anti-gingivitis agents. Stannous fluoride is known in particular for its enamel hardening effects. Sanguinarine and chlorhexidine digluconate are known to be antiplaque agents. The soluble pyrophosphates are said to minimize newly-formed calculus Other dentally-active agents may be used as well.

The dentally-active pharmacological agent may itself be water-soluble, as are the halide salts, the soluble pyrophosphates, and chlorhexidine digluconate, or substantially water insoluble, as are sanguinarine and the phenolic compounds such as eugenol. During blending and formation of the polymeric orthodontic member, the agents may be added directly to the polymeric material as the sole material to be dispersed, or may be mixed with other carriers or other materials to form a composition to be dispersed in the polymeric material.

While water solubility of the dispersed composition may be important in some applications, such that saliva will serve to facilitate release of the composition from the polymeric orthodontic member, in other applications adequate release for the intended purposes can be attained even though the dispersed composition is water-insoluble.

The dispersed composition may comprise or consist of a carrier composition and the dentally-active pharmacological agent (whether water soluble or insoluble) which is dissolved in it. In some cases such carrier composition may be a solvent for a water-insoluble dentally-active agent, such as sanguinarine, and itself be soluble in water to aid release. A good example of such a carrier is propylene glycol.

Release of the dispersed composition may serve multiple purposes. For example, the dispersed composition may carry a flavoring oil as well as the dentally-active agent. This may serve to mask any unpleasant taste of the dentally-active agent. In some cases, the dispersed composition may carry two or more dentally-active agents, serving one or more therapeutic purposes.

The dispersed composition may have additional constituents serving a variety of purposes.

Among such additional constituents are fillers having various purposes. Certain fillers, including clay fillers such as barium sulfate and calcium carbonate, may be added for increased porosity. These fillers may be included in the composition dispersed in polyurethane, for example, in amounts of up to about 20 parts by weight per 100 parts of polyurethane. Silicate fillers may be included to increase abrasion resistance in the elastic orthodontic members. Such fillers may be added in amounts of up to about 30 parts by weight per 100 parts of polymeric material.

To increase extrusion rates and reduce blocking tendencies, powdered polyolefins or natural/synthetic waxes can be incorporated into the dispersed composition. In some cases, polycarboiimides may be added to improve the hydrolytic stability of the polyether.

The polymeric elastic orthodontic members may be used in the following manner:

Such improved polymeric elastic members are placed in the mouth and attached to teeth, orthodontic braces, hooks, or other orthodontic paraphernalia in the same manner as similar old-style forms have heretofore been used. The pharmacological agents are released from such elastic orthodontic members over an extended period and are carried by the oral fluids to contact the teeth and gingiva in efficacious amounts. The period of pharmacological agent release is substantially commensurate with the period of useful force-applying life of the orthodontic member in a patient's mouth.

Some of such polymeric elastic orthodontic members, such as elastic bands, are removed and replaced by the patient frequently in order to maintain desired levels of tension for orthodontic reasons. The used elastic orthodontic members are replaced with unused members to provide a continuous fresh supply of pharmacological agents. Such members are made to release dentally-active agents at acceptable low concentrations over fairly short periods, corresponding approximately with the intended duration of use.

Other polymeric elastic orthodontic members are changed less frequently, typically by the orthodontist during weekly or biweekly visits. Such members are made to release dentally-active agents at a much lower rate and over a longer time, again commensurate with the force-applying life of the material. Still other elastic orthodontic members are kept in the mouth for longer periods, and have dentally-active agents incorporated for more extended release.

Various methods may be used to make the polymeric elastic orthodontic members of this invention. The choice of an acceptable method will depend in part on the nature of the orthodontic member to be made, that is, whether is an elastic band, an elastomeric chain, etc.

The process typically will involve: a blending step in which the composition to be dispersed is blended with the orally-acceptable elastic polymeric material; a heat-forming step, such as extrusion, molding, or dipping, to name some well-known processes, in which the elastic polymeric material and dispersed composition are joined to form a homogeneous body of the desired shape or an intermediate shape; and, in many cases, a final mechanical step, such as cutting, punching, or trimming, to produce the improved polymeric elastic orthodontic member in its final form.

Production processes for each individual form of polymeric elastic orthodontic member of this invention will not be described; rather, by way of example, certain methods will be described for manufacture of elastomeric chains and elastic bands in accordance with this invention.

As with other elastic bands, long elastic tubes are first formed and then cut by automatic cutters to form the bands. For elastomeric chains, flat bands or sheets are first made and then punched and cut to provide the desired form. Other polymeric orthodontic members will be formed with heat-forming steps and in some cases later mechanical forming steps as known in the orthodontic implement art.

The long tubes from which elastic bands are cut may be made by a dipping process or an extruding process. In the dipping process, the curing may, for example, be carried out using continuous hot air tunnels or radiant heat. In the extruding process, a hot liquid cure or fluidized bed may be used.

A preferred method of making the tubes involves a dipping process which is carried out as follows:

A liquid rubber latex is placed in a suitable tank or other mixing vessel which has an agitator or other mixing device in it. Suitable vulcanizing agents, accelerators, activators, emulsion stabilizers, and anti-oxidants are blended into the natural rubber latex. This is carried out in known manner.

The dentally-active agent is separately prepared for blending into the latex mixture. Such agent may be alone in very fine powder or liquid form, or an intermediate may be made in a separate vessel by mixing the dentally-active agent(s) together with carrier fluids, such as water, oils (including flavoring oils), and perhaps emulsifiers. Such agent or intermediate containing such agent is then added to the latex mixture and blended thoroughly. The amount of the agent and the nature of the carrier fluid are chosen to allow the desired release properties.

A flexible mandril, for example, a silicone snake having a generally uniform outer diameter which is equal to the intended, non-expanded inner diameter of the elastic band to be made, is dipped repeatedly into the above final blend. Each time the mandrel emerges from the blend, heat is applied to it, which gels the adhering material. The heat is preferably applied by infrared heaters.

About 0.002 inch of material thickness is added to the mandril per dip, the amount depending on various factors, primarily including the nature of the blend. For an orthodontic elastic band having about an 0.032 inch wall dimension, 16 dips are required. After the last dip and the brief period of heat application to gel the last dip, the formed tube is stripped from the mandril, usually by applying high-pressure air at one end of the mandril.

This tube may then be passed through a bromine bath, with the ends of the tube preferably being tied such that only the outside surface of the tube is exposed to the bromine bath. The bromine bath serves to react with any unsaturated double bonds to reduce tackiness on the outside of the tube. Then, the tube is passed, depending on the nature of the dispersed composition, into either a hot liquid or a fluidized bed for a final cure. After removal from such curing medium, the tube may be dried, and then is ready for cutting with automatic cutting equipment.

The extrusion method, which typically uses a very high temperature (140–200 degrees C.) cure, has the advantage of higher production rates. Extrusion methods are well known to those skilled in the art. Such method may be described by giving an example used in connection with manufacture of elastomeric chains, as follows:

An acceptable polyether-type urethane or natural rubber is dry-mixed with stannous fluoride, for example, in a Banbury type mixer or a two-roll mill. After substantial mixing, the mixture is run through an extruder to form an extrusion of any cross-sectional shape. Such extrusion is then ground, the grindings remixed, and the remixed grindings then run through an extruder again, this time with the extruder having an extrusion opening dimensioned to match the widest cross-section of the desired elastomeric chain, or some multiple of the chain width.

Double extrusion serves to more uniformly disperse the stannous fluoride in the polymeric elastic member. But, depending on the mixing procedures, double extrusion may not be required; single extrusion with more vigorous blending is quite acceptable.

In the last extrusion step, a solid extrusion of the desired intermediate shape flows out of the extruder. The extrusion may then be run through a mechanical device for edge trimming, die-cutting and hole punching to reach the desired shape and form for a elastomeric chain.

A wide variety of other methods for the preparation of various polymeric elastic orthodontic members of this invention may be used. Acceptable methods would be apparent to those skilled in the art who are familiar with this invention.

EXAMPLES

In each example which follows, the compositions are blended and then the polymeric elastic members heat-formed and cut using the methods described above. In each case the composition will include the listed ingredients. Amounts are given in parts by weight.

EXAMPLE 1

An orthodontic elastic band having a 0.032 inch wall dimension and a 0.25 inch unexpanded diameter (when in circular form) is made using dipping and cutting methods as described above with a dipping blend made as follows:

| Ingredient | Amount (in parts) |
|---|---|
| Polyisoprene latex | 100.00 |
| Stannous fluoride | 6.40 |
| Anionic stabilizer | 0.50 |
| Dibutyl ammonium oleate | 0.75 |
| Antioxidant | 2.00 |
| Zinc oxide | 0.50 |
| Sulfur | 1.50 |
| Accelerator | 0.50 |
| Givaudan F8266 flavoring | 4.00 |

The resulting orthodontic rubber band, when in use, will release pharmacologically-useful amounts of stannous fluoride into the saliva. The flavoring substance, an artificial spearmint oil, is optional. The elastic bands provide good corrective force in tension, as required of orthodontic rubber bands.

EXAMPLES 2–5

Elastic bands having a 0.032 inch wall dimension and a inch unexpanded diameter are made as in Example 1, with the same ingredients except that stannous fluoride is replaced by the following dentally-active agents:

| Example No. | Agent(s) | Amount (parts) |
|---|---|---|
| 2 | Domiphen bromide | 1.0 |
| 3 | Chlorhexidine gluconate | 0.2 |
| 4 | Tetrasodium pyrophosphate | 3.5 |
|   | Disodium dihydrogen pyrophosphate | 1.5 |
|   | Sodium fluoride | 0.25 |
| 5 | Benzalkonium chloride | 5.0 |

The resulting orthodontic rubber bands release useful amounts of dentally-active agents into the saliva.

EXAMPLE 6

An elastomeric chain is made by extrusion and mechanical forming methods as described above, curing in a temperature range of 140–180 degrees C., using the following blend:

| Ingredient | Amount (in parts) |
|---|---|
| Natural rubber (pale crepe) | 100.00 |
| Stannous fluoride | 1.50 |
| Stearic acid | 0.75 |
| Zinc oxide | 0.75 |
| Antioxidant | 1.00 |
| Accelerator | 1.00 |
| Curing agent | 1.25 |

The resulting elastomeric chain, when in use, will release pharmacologically-useful amounts of stannous fluoride into the saliva, continuously over an extended period. The elastomeric chain, while releasing stannous fluoride for protective purposes, functions in every other respect in the normal manner of orthodontic elastomeric chains.

EXAMPLES 7–10

Elastomeric chains are made as in Example 6, with the same ingredients except that stannous fluoride is replaced by the following dentally-active agents:

| Example No. | Agent(s) | Amount (parts) |
|---|---|---|
| 7 | Domiphen bromide | 1.0 |

-continued

| Example No. | Agent(s) | Amount (parts) |
|---|---|---|
| 8 | Chlorhexidine gluconate | 0.2 |
| 9 | Tetrasodium pyrophosphate | 3.5 |
|   | Disodium dihydrogen pyrophosphate | 1.5 |
|   | Sodium fluoride | 0.25 |
| 10 | Benzalkonium chloride | 5.0 |

The resulting orthodontic elastomeric chains release useful amounts of dentally-active agents into the saliva during their use. The chlorhexidine digluconate provides a continuous antiplaque effect in the mouth over an extended period. The soluble pyrophosphate mixture with sodium chloride provides a continuous anti-calculus effect. The benzalkonium chloride provides a continuing antiseptic effect minimizing the creation of conditions in the mouth which lead to dental disease.

The same methods, with changes only to accommodate the different mechanical shapes, can be used to make elastomeric ties and threads, separators, Steiner rotation wedges, and the like.

Other molding methods can be used. Suitable production methods for each of the polymeric elastic orthodontic members would be apparent to those skilled in the art who are made familiar with this invention.

EXAMPLES 11

Another elastomeric chain is made as in Example 6, with the same ingredients except that stannous fluoride is replaced by one part of a 1.0% (by weight) solution of sanguinarine in propylene glycol. The resulting elastomeric chain releases sanguinarine in amounts producing a very low concentration thereof in the saliva during use of the elastomeric chain.

EXAMPLE 12

An elastomeric chain is made using 100 parts of PELLATHANE 2363-75A and 10 parts eugenol. The extrusion and mechanical forming steps described above are used. The resulting elastomeric chain continuously delivers an analgesic agent to the mouth over a substantial period.

EXAMPLE 13

A super tie is made using 100 parts of PELLATHANE 2363-75A, 3 parts tetrasodium pyrophosphate, and 2 parts sodium chloride. An extrusion method as described above is used, with the extrusion being a tube of narrow diameter. No mechanical steps are required after final extrusion. The resulting super tie continuously delivers an anti-calculus agent to the mouth over a substantial period.

EXAMPLE 14

An elastomeric chain is made using 100 parts of PELLATHANE 2363-75A, 1.5 parts stannous fluoride, and 30 parts calcium silicate. The extrusion and mechanical forming steps described above are used. The resulting elastomeric chain continuously delivers an anticaries and anti-gingival effect into the mouth over a substantial period. The elastomeric chain has good abrasion resistance.

EXAMPLE 15

An orthodontic super tie is made using an extrusion method as described above with materials as follows:

| Ingredient | Amount (in parts) |
|---|---|
| Neoprene | 100.00 |
| Stannous fluoride | 1.50 |
| Antioxidant | 2.00 |
| Zinc oxide | 5.00 |
| Magnesium oxide | 2.00 |
| Accelerator | 1.00 |
| Plasticizer | 20.00 |

The extrusion is in the form of a tube of narrow diameter. No mechanical steps are required after final extrusion. The resulting super tie continuously releases a pharmacologically-useful amounts of stannous fluoride into the saliva over an extended period.

While the principles of this invention have been described in connection with specific embodiments, it should be understood clearly that these descriptions are made only by way of example and are not intended to limit the scope of the invention.

We claim:

1. A method for prevention and treatment of dental disease during a course of orthodontic treatment comprising:

mounting under tension in orthodontic force-applying positions, at treatment locations within the mouth, at least one force-applying polymeric elastic orthodontic member, the elastic member being an orally-acceptable substantially water-insoluble elastic polymeric material selected from the group consisting of natural rubbers, natural-synthetic rubbers, synthetic rubbers, and thermoplastic polymeric materials, and blends thereof, having suitable physical properties, with a dentally-active pharmacological agent uniform throughout the elastic polymeric material as an in situ constituent of polymeric-member formation from a homogeneous mixture of said polymeric material and said pharmacological agent, the elastic polymeric material having dispersed therein a composition which includes the pharmacological agent, such dispersed composition being present in an amount no more than about 30 parts by weight per 100 parts of the elastic polymeric material;

releasing the dentally-active pharmacological agent throughout the useful force-applying life of the polymeric elastic member, such release being where most needed and in therapeutically-acceptable concentrations, by maintaining said force-applying polymeric elastic member(s) at said orthodontic treatment location(s); and at a time after the mounting step, removing and discarding the elastic orthodontic member and replacing it with an unused similar elastic orthodontic member, thereby to enhance continuous application of the dentally-active agent;

whereby protection against or treatment of dental disease is provided without compromising orthodontic force-applying elasticity of the orthodontic member, the protection provided by each such orthodontic member being provided over an extended period which is substantially commensurate with the useful life of force-applying elasticity of said orthodontic member.

2. The method of claim 1 wherein the pharmacological agent itself is water-soluble.

3. The method of claim 1 wherein the dispersed composition comprises a carrier composition in which the pharmacological agent is dissolved.

4. The method of claim 3 wherein the pharmacological agent itself is water-soluble.

5. The method of claim 3 wherein the pharmacological agent itself is substantially water-insoluble.

6. The method of claim 5 wherein the carrier composition comprises propylene glycol.

7. The method of claim 1 wherein the dispersed composition also includes a flavoring oil.

8. The method of claim 1 wherein the pharmacological agent is selected from the group consisting of halide salts, chlorhexidine digluconate, soluble pyrophosphates, sanguinarine, quaternary ammonium antiseptics, phenolic compounds, and mixtures thereof.

9. The method of claim 1 wherein the pharmacological agent is selected from the group consisting of stannous fluoride, sodium fluoride, sodium chloride, domiphen bromide, tetrasodium pyrophosphate, disodium dihydrogen pyrophosphate, and mixtures thereof.

* * * * *